United States Patent [19]

Szantay et al.

[11] 4,343,738

[45] * Aug. 10, 1982

[54] HALOGENATED 15-HYDROXY-E-HOMOEBURANE DERIVATIVES

[75] Inventors: Csaba Szantay; Lajos Szabo; György Kalaus; Lajos Dancsi; Tibor Keve; Ferenc Drexler, all of Budapest, Hungary

[73] Assignee: Richter Gedeon Vegyeszeti Gyar Rt., Budapest, Hungary

[*] Notice: The portion of the term of this patent subsequent to Aug. 25, 1998, has been disclaimed.

[21] Appl. No.: 216,903

[22] Filed: Dec. 16, 1980

Related U.S. Application Data

[63] Continuation-in-part of Ser. No. 175,385, Aug. 5, 1980, Pat. No. 4,285,865, and a continuation-in-part of Ser. No. 168,560, Jul. 14, 1980, Pat. No. 4,314,939.

[30] Foreign Application Priority Data

Aug. 6, 1979 [HU] Hungary ................. RI-721

[51] Int. Cl.³ .............................. C07D 471/22
[52] U.S. Cl. ............................... 260/239.3 P
[58] Field of Search ............... 260/239.3 P, 244.4

[56] References Cited

FOREIGN PATENT DOCUMENTS

| | | | |
|---|---|---|---|
| 765006 | 3/1971 | Belgium | 260/239.3 P |
| 2458164 | 6/1975 | Fed. Rep. of Germany | 546/51 |
| 2928187 | 1/1980 | Fed. Rep. of Germany | 260/239.3 P |

OTHER PUBLICATIONS

Laronze et al. "Bulletin de la Societe Chimique de France" (1977) No. 11-12 pp. 1207-1214.

*Primary Examiner*—Robert T. Bond
*Attorney, Agent, or Firm*—Karl F. Ross

[57] ABSTRACT

The invention relates to new, racemic or optically active, halogenated 15-hydroxy-E-homoeburnane derivatives of the formulae (Ia) and/or (Ib),

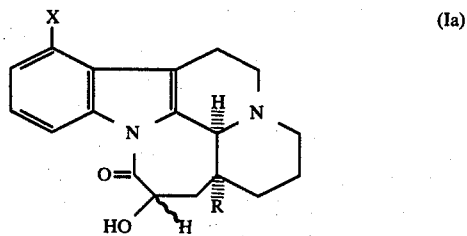

(Ia)

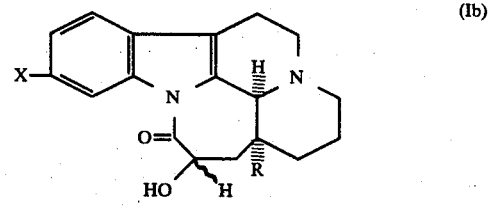

(Ib)

wherein R is a $C_{1-6}$ alkyl group and X is halogen, and acid addition salts thereof. These compounds are biologically active, furthermore they can be applied as intermediates in the synthesis of other pharmaceutically active substances.

5 Claims, No Drawings

HALOGENATED 15-HYDROXY-E-HOMOEBURANE DERIVATIVES

This application is a continuation-in-part of copending Ser. No. 175,385 filed Aug. 5, 1980 now U.S. Pat. No. 4,285,865 and is a continuation-in-part of Ser. No. 168,560 filed July 14, 1980, now U.S. Pat. No. 4,314,939.

The invention relates to new, racemic or optically active, halogenated 15-hydroxy-E-homoeburnane derivatives of the formulae (Ia) and/or (Ib),

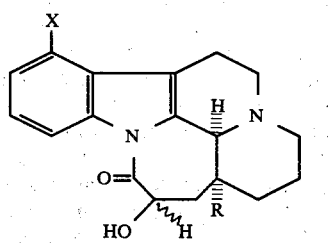

wherein R is a $C_{1-6}$ alkyl group and X is halogen, and acid addition salts thereof, furthermore to a process for the preparation of these new compounds.

The new compounds defined above are prepared according to the invention so that a racemic or optically active 15-hydroxy-E-homoeburnane derivative of the formula (II),

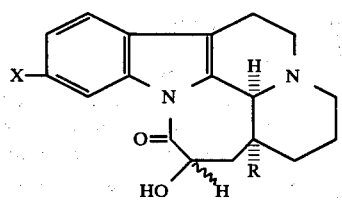

wherein R is as defined above, or an acid addition salt thereof is treated with a halogenating agent. If desired, the compounds of the formulae (Ia) and (Ib) formed in the reaction are separated from one another, and then either of the compounds is converted into its acid addition salt and/or resolved, if desired.

The new compounds according to the invention can be utilized as intermediates in the preparation of pharmaceutically active compounds, such as halovincaminic acid esters. The new compounds according to the invention also possess valuable biological effects.

In the compounds of the formulae (Ia) and (Ib) R may represent a straight-chain or branched $C_{1-6}$ alkyl group, such as methyl, ethyl, n-propyl, isopropyl, n-butyl, sec.-butyl, tert.-butyl, n-pentyl, isopentyl, n-hexyl or isohexyl group. R is preferably an ethyl or n-butyl group.

X may represent all the four halogens, i.e. fluorine, chlorine, bromine and iodine, preferably bromine.

The starting substances of the formula (II) can be prepared by the method described in Tetrahedron 33, 1803 (1977).

The starting substances of the formula (II) are halogenated with reactants capable of introducing a halogen atom into the unsaturated ring without simultaneously replacing the 15-hydroxy-group by a halogen. It is preferred to use elemental halogens as halogenating agents.

According to a preferred method of the invention compounds of the formulae (Ia) and (Ib) in which X stands for bromine are prepared. The corresponding starting substances of the formula (II) are brominated preferably with elementary bromine, but other brominating agents leading to the formation of the required bromo compound can also be used.

Bromination is performed in an inert organic solvent or solvent mixture. Of the solvents usable in this step, e.g. the following are to be mentioned: non-polar organic solvents, such as halogenated aliphatic hydrocarbons (e.g. chloroform, dichloromethane, dichloroethane, etc.), furthermore polar organic solvents, such as organic acids (e.g. glacial acetic acid, propionic acid, etc.).

In some instances it is preferred to perform bromination in the presence of a Lewis acid. As the Lewis acid e.g. ferric chloride, zinc chloride, aluminum chloride, stannic chloride, antimony tetrachloride, boron trifluoride, etc. can be used.

Bromination can be performed at temperatures of 20° to 40° C., preferably at room temperature.

The ratio of the stereoisomers formed in the reaction depends on the rate of bromine administration.

When brominating a compound of the formula (II), a mixture of the compounds of the formulae (Ia) and (Ib) is obtained. The two stereoisomer bromo derivatives can be separated from one another by methods known per se, such as crystallization, salt formation and separation, or preparative layer chromatography. It is preferred to use Merck $PF_{254+366}$ grade silica gel as adsorbent in the preparative layer chromatography. Various solvent combinations can be utilized as running and eluting agents.

The compounds of the formulae (Ia) and/or (Ib) can be reacted with various acids to form the respective acid addition salts. Of the acids applicable in this reaction, e.g. the following are to be mentioned: mineral acids, such as hydrogen halides (e.g. hydrochloric acid or hydrogen bromide), sulfuric acid, phosphoric acid, nitric acid, perhaloic acids (e.g. perchloric acid), etc., organic carboxylic acids, such as formic acid, acetic acid, propionic acid, glycolic acid, maleic acid, hydroxymaleic acid, fumaric acid, salicylic acid, lactic acid, cinnamic acid, benzoic acid, phenylacetic acid, p-aminobenzoic acid, p-hydroxybenzoic acid, p-aminosalicyclic acid, etc., alkylsulfonic acids, such as methanesulfonic acid, ethanesulfonic acid, etc., cycloaliphatic sulfonic acids, such as cyclohexylsulfonic acid, arylsulfonic acids, such as p-toluenesulfonic acid, naphthylsulfonic acid, sulfanylic acid, etc., amino acids, such as aspartic acid, glutamic acid, etc.

If desired, the racemic compounds of the formulae (Ia) and/or (Ib) can be resolved in a manner known per se to obtain the respective optically active derivatives. Optically active end products can also be obtained, however, when an optically active compound of the formula (II) is applied as the starting substance.

If desired, the racemic or optically active compounds of the formulae (Ia) and/or (Ib), as well as the acid addition salts thereof can be subjected to further purification steps, such as recrystallization from an appropriately selected solvent or solvent mixture. The solvents or solvent mixtures utilized in this step are chosen in accordance with the solubility and crystallization characteristics of the substance to be purified.

The process of the invention yields the end-products in forms easy to identify. The IR spectra, NMR spectra and mass spectra of the compounds prepared are in harmony with the assigned structures.

The 9- or 11-halogen-14-oxo-15-hydroxy-E-homoeburnane of the formulae (Ia) or (Ib) is treated with a halogenating agent (in the way disclosed in copending application Ser. No. 168,560, now U.S. Pat. No. 4,314,939 issued Feb. 9, 1982), preferably with phosphorus oxychloride and the thus obtained 9- or 11-halogen-14-oxo-15-halogen-E-homoeburnane is reacted with an alkali metal nitrite (e.g. sodium nitrite). The resulting 9- or 11-halogen-14-oxo-15-hydroxy-imino-E-homoeburnane is transformed in a known way, e.g. by the methods disclosed in Belgian Pat. No. 765,006 issued Sept. 30, 1971, into the corresponding halovincaminic acid ester, e.g. into the bromo-vincamine having cerebral vasodilating effects, disclosed in German patent application No. 2,458,164 published June 26, 1975.

Specifically the compound of the formulae (Ia) or (Ib) is treated, optionally after separating the 15-epimers from one another, with a halogenating agent and the resulting 15-halo-E-homoeburnane of the formula (III)

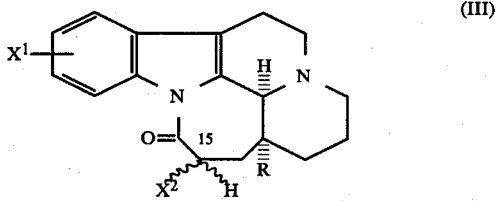

(III)

wherein R is as defined above, $X^1$ is a 9- or 11-halogen, and $X^2$ is halogen, is reacted, optionally after separating the individual epimers from one another, with an alkali metal nitrite in the presence of an acid to yield a 15-hydroxy-imino-E-homoeburnane of the formula (IV):

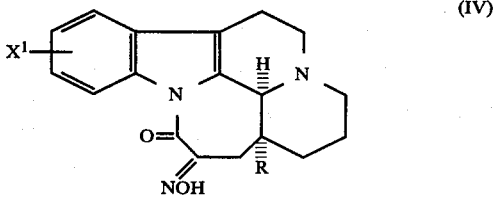

(IV)

If desired, the compounds of the formula (IV) can be converted into their acid addition salts and/or resolved.

The compounds of the formula (IV) are valuable intermediates applicable in the preparation of compounds with outstanding pharmacological properties, such as apovincaminic acid ethyl ester, vincamine, 11-bromo-vincamine, etc. The compounds of formula (IV) in which $X^1$ is bromo and R is ethyl can be converted into a 9- or 11-bromovincamine by subjecting said compounds to deoxomation and treating the resulting compound with a base in the presence of an alcohol. See German published specification No. 2,928,187 published Jan. 24, 1980. Furthermore compounds of the formula (IV) in which $X^1$ is bromo or themselves biologically active.

The compounds of formulae (Ia) or (Ib) can be utilized in a process to produce compounds of formulae (III) and (IV) directly as the mixtures of 15-epimers formed in the above processes, without any purification. One can also subject, however, the crude mixture of 15-epimers first to an epimerization step, which also involves a certain degree of purification, and conduct then the process of the invention with any of the pure epimers.

Epimerization can be performed by recrystallizing the crude mixture of 15-epimers from methanol. This operation also serves as purification, since, beside the undesired epimer, any other contaminants, such as starting substances, intermediates, decomposition products, etc., are removed as well. The solid product of recrystallization is one of the epimers; the other epimer can be separated from the mother liquor by preparative layer chromatography, utilizing silica gel as an adsorbent and a 14:3 mixture of benzene and methanol as eluent.

Racemic and optically active compounds of the formulae (Ia) or (Ib) can equally be applied as starting substances in the process to form compounds of formula (III) and (IV).

When converting the compounds of the formulae (Ia) or (Ib) into the respective 15-halo derivatives of the formula (III), halogenating agents capable of exchanging an alcoholic or phenolic hydroxy group to halogen without simultaneously halogenating the aromatic ring are applied. Of these halogenating agents e.g. halides and oxyhalides of phosphorus or sulfur, such as phosphorous oxychloride, phosphorous trichloride, phosphorous pentachloride, thionyl chloride, phosphorous pentabromide, phosphorous tribromide, etc., are to be mentioned.

Halogenation is performed in the presence of an inert organic solvent, preferably in an optionally substituted aromatic hydrocarbon. The preferred solvent is chlorobenzene.

Halogenation is performed at elevated temperatures, preferably at the boiling point of the reaction mixture. Under such conditions the reaction proceeds within some hours, preferably within 1 to 5 hours.

The compounds of the formula (III) obtained in this halogenation step are also mixtures of the respective 15-epimers. It is not necessary to separate the individual epimers from each other in this step, since in the next step of the synthesis the center of asymmetry in position 15 is eliminated. However, if desired, the individual epimers can be separated from each other by preparative layer chromatography, since they have different $R_f$ values.

The compounds of the formula (III), are new substances and possess biological activities, in their own right, as well as being useful as intermediates to produce compounds of formula (IV).

The compounds of the formula (III) are converted into the end-products of the general formula (IV) by reacting them with an alkali nitrite in the presence of an acid. This reaction can be performed in the presence of a solvent, but the excess of the acid solution can also serve as reaction medium. The alkali nitrite, such as potassium or sodium nitrite, can be introduced as an aqueous solution. The acids usable in this step include organic acids, such as acetic acid, and mineral acids, furthermore aqueous solutions thereof (e.g. 1 n hydrochloric acid solution) are to be mentioned. Water-miscible solvents, such as alcohols, dimethyl formamide, dimethyl sulfoxide, dioxane, tetrahydrofuran, etc., and water-immiscible solvents, such as dichloromethane, can also be used as reaction media, and the reaction can also be performed in the excess of the acidic solution.

According to a preferred method the compounds of the formula (III) are treated with an aqueous solution of sodium nitrite in acetic acid. The reaction is performed preferably at room temperature.

The above reaction yields the end-products of the formula (IV) in the form of the free bases. If desired, the free bases can be converted into their acid addition salts utilizing the organic or mineral acids listed above. The salts are generally crystalline solids, easy to identify.

If desired, the compounds of the formula (IV) can be subjected to further purification steps, such as recrystallization from an appropriately selected solvent. As solvent a dialkyl ether, such as diethyl ether, can be used.

If desired, the racemic compounds of the formula (IV) can be resolved by methods known per se.

The invention is elucidated in detail by the aid of the following non-limiting Examples.

EXAMPLE 1

($\pm$)-9-Bromo-14-oxo-15-hydroxy-E-homoeburnane-(3$\alpha$,17$\alpha$) and
($\pm$)-11-bromo-14-oxo-15-hydroxy-E-homoeburnane-(3$\alpha$,17$\alpha$).

(a) 1.1 g of ferric chloride hexahydrate are added to a solution of 1.30 g (4.01 mmoles) of ($\pm$)-14-oxo-15-hydroxy-E-homoeburnane-(3$\alpha$,17$\alpha$), melting at 193°–195° C., in 15 ml of glacial acetic acid, and 5 ml of a 1 molar bromine solution in glacial acetic acid are added dropwise to the mixture at room temperature under constant stirring. The bromine solution is introduced slowly, at a rate of 0.5 ml/min. When the addition is complete the mixture is stirred for an additional 9 hours at room temperature. When the reaction terminates 200 ml of water are added to the suspension, and the pH of the resulting mixture is adjusted to 5 with 25% aqueous ammonia. The mixture is extracted with 100, 80 and 60 ml of dichloromethane. The organic solutions are combined, admixed with 100 ml of water, and the pH of the mixture is adjusted to 10 with 25% aqueous ammonia. The two-phase mixture is shaken, thereafter the dichloromethane phase is separated, washed thrice with 100 ml of water, each, dried over anhydrous solid magnesium sulfate, filtered, and the filtrate is evaporated to dryness in vacuo.

The 1.4 g of dry residue obtained are subjected to preparative thin layer chromatography. Kieselgel PF$_{254+366}$ grade silica gel plates, 20$\times$20 cm in area and 1.5 mm in thickness, are applied as adsorbent, and a 10:3 mixture of benzene and acetonitrile is applied as solvent. The eluted substances are crystallized from methanol.

0.15 g (11%) of ($\pm$)-9-bromo-14-oxo-15-hydroxy-E-homoeburnane-(3$\alpha$,17$\alpha$), are isolated from the upper spot. The substance melts at 202°–203° C. The empirical formula of the product is C$_{20}$H$_{23}$BrN$_2$O$_2$ (mol.wt.: 403.33).

IR spectrum (KBr): $\nu_{max}$. 3410 cm$^{-1}$ (—OH), 1685 cm$^{-1}$ (amide—CO).

NMR spectrum (deuterochloroform): $\delta$=0.97 (t, 3H, CH$_3$). 7.21-8.64 (m, 3H, aromatic protons).

C$_{10}$—H=7.51 ppm, J$_{11,12}$=7.8 H (ortho)
C$_{11}$—H=7.21 ppm, J$_{11,10}$=7.6 Hz (ortho)
C$_{12}$—H=8.64 ppm, J$_{10,12}$=1.9 Hz (meta).

Mass spectrum (m/e): 404, 403, 402, 401, 376, 374, 360, 358, 347, 345, 332, 330, 317, 315, 303, 301, 277, 275, 180, 167, 153, 140.

0.63 g (46.1%) of ($\pm$)-11-bromo-14-oxo-15-hydroxy-E-homoeburnane-(3$\alpha$,17$\alpha$) are isolated from the middle spot. The substance melts at 195°–197° C. The empirical formula of the product is C$_{20}$H$_{23}$BrN$_2$O$_2$ (mol.wt.: 403.33).

IR spectrum (KBr): $\nu_{max}$. 3350 cm$^{-1}$ (—OH), 1680 cm$^{-1}$ (amide—CO).

NMR spectrum (deuterochloroform): $\delta$=0.95 (t, 3H, CH$_3$), 7.25-8.69 (m, 3H, aromatic protons) ppm.

C$_9$—H=7.25 ppm, J$_{10,12}$=1.9 Hz (meta)
C$_{10}$—H=7.39 ppm, J$_{10,9}$=7.7 Hz (ortho)
C$_{12}$—H=8.69 ppm, J$_{9,12}$=0.3 Hz (para)

Mass spectrum (m/e): 404, 403, 402, 401, 376, 374, 360, 358, 347, 345, 332, 330, 317, 315, 303, 301, 277, 275, 180, 167, 153, 140.

0.2 g of the starting substance, ($\pm$)-14-oxo-15-hydroxy-E-homoeburnane-(3$\alpha$,17$\alpha$) are recovered from the lower spot.

(b) 1.1 g of ferric chloride hexahydrate are added to a solution of 1.3 g (4.01 mmoles) of ($\pm$)-14-oxo-15-hydroxy-E-homoeburnane-(3$\alpha$,17$\alpha$), melting at 193°–195° C., in 15 ml of glacial acetic acid, and 5 ml of a 1 molar bromine solution in glacial acetic acid are added to the mixture in a single portion at room temperature under constant stirring. The reaction mixture is stirred at room temperature for an additional 9 hours; thereafter it is diluted with 200 ml of water, and the pH of the aqueous phase is adjusted to 5 with 25% aqueous ammonia. The mixture is extracted then with 100, 80 and 60 ml of dichloromethane. The organic phases are combined, admixed with 100 ml of water, and the pH of the aqueous phase is adjusted to 10 with 25% aqueous ammonia. The mixture is shaken, the dichloromethane phase is separated, washed thrice with 100 ml of water, each, dried over anhydrous solid magnesium sulfate, filtered, and the filtrate is evaported to dryness in vacuo. The 1.5 g of dry residue obtained are subjected to preparative thin layer chromatography. Kieselgel PF$_{254+366}$ grade silica gel plates, 20$\times$20 cm in area and 1.5 mm in thickness, are applied as adsorbent, and a 10:3 mixture of benzene and acetonitrile is applied as solvent. The eluted substances are crystallized from methanol.

0.2134 g (13.2%) of ($\pm$)-9-bromo-14-oxo-15-hydroxy-E-homoeburnane-(3$\alpha$,17$\alpha$) are isolated from the upper spot. This substance (the product with the higher R$_f$ value) is identical with the compound of the highest R$_f$ value prepared as described in point (a).

0.6684 g (41.4%) of ($\pm$)-11-bromo-14-oxo-15-hydroxy-E-homoeburnane-(3$\alpha$,17$\alpha$), a product with lower R$_f$ value, are isolated from the middle spot. This substance is identical with the compound of the medium R$_f$ value prepared as described in point (a).

9-Bromo-14,15-dioxo-E-homoeburnane-(3$\alpha$,17$\alpha$) and 11-bromo-14,15-dioxo-E-homoeburnane-(3$\alpha$,17$\alpha$) are also formed in the reaction in an amount of about 5%. These compounds were identified by thin layer chromatography.

EXAMPLE 2

(+)-3(S),17(S)-9-Bromo-14-oxo-15-hydroxy-E-homo-eburnane and
(+)-3(S),17(S)-11-bromo-14-oxo-15-hydroxy-E-homo-eburnane 1.10 g of ferric chloride hexahydrate are added to a solution of 1.45 g (4.02 mmoles) of (+)-3(S),17(S)-14-oxo-15-hydroxy-E-homoeburnane hydrochloride (m.p.: 240°–242° C.; $[\alpha]_D^{20} = +37.8°$, c=1%, in pyridine) in 15 ml of glacial acetic acid, and 5 ml of a 1 molar bromine solution in glacial acetic acid are added slowly, at a rate of 0.5 ml/min., to the solution at room temperature under constant stirring. When the addition is complete the mixture is stirred for an additional 9 hours at room temperature. When the reaction terminates the mixture is diluted with 200 ml of water, and the pH of the mixture is adjusted to 5 with 25% aqueous ammonia. The resulting solution is extracted with 100, 80 and 60 ml of dichloromethane. The organic phases are combined, admixed with 100 ml of water, and the pH of the aqueous phase is adjusted to 10 with 25% aqueous ammonia. The mixture is shaken, the dichloromethane phase is separated, washed thrice with 100 ml of water, each, dried over solid anhydrous magnesium sulfate, filtered, and the filtrate is evaporated in vacuo.

The 1.4 g of dry residue obtained are subjected to preparative thin layer chromatography, Kieselgel PF$_{254+366}$ grade silica gel plates, 20×20 cm in area and 1.5 mm in thickness, are applied as adsorbent, and a 10:3 mixture of benzene and acetonitrile is applied as solvent. The eluted substances are crystallized from methanol.

The substance with the higher $R_f$ value is (±)-3(S),17(S)-9-bromo-14-oxo-15-hydroxy-E-homo-eburnane. This compound is obtained with a yield of 0.2 g (12.3%) and melts at 104°–105° C. The empirical formula of the substance is $C_{20}H_{23}BrN_2O_2$ (mol.wt.: 403.33).

IR spectrum (KBr): $\nu_{max}$. 3380 cm$^{-1}$ (—OH), 1690 cm$^{-1}$ (—CO).

$[\alpha]_D^{20} = +43.7°$ (c=1%, in chloroform).

The substance with the lower $R_f$ value is (+)-3(S),17(S)-11-bromo-14-oxo-15-hydroxy-E-homo-eburnane. This compound is obtained with a yield of 0.8 g (49.4%) and melts at 117°–119° C. The empirical formula of the substance is $C_{20}H_{23}BrN_2O_2$ (mol.wt.: 403.33).

IR spectrum (KBr): $\nu_{max}$. 3350 cm$^{-1}$ (—OH), 1680 cm$^{-1}$ (—CO).

$[\alpha]_D = +18.3°$ (c=1%, in chloroform).

EXAMPLE 3

(+)-3(S),17(S)-11-Bromo-14-oxo-15-chloro-E-homo-eburnane (mixture of 15-epimers).

A solution of 0.85 g of phosphorous oxychloride in 1 ml of chlorobenzene is added to a stirred solution of 1.00 g (2.48 mmoles) of (+)-3(S),17(S)-11-bromo-14-oxo-15-hydroxy-E-homoeburnane (mixture of 15-epimers) in 19 ml of chlorobenzene, and the resulting mixture is refluxed for 2 hours. The raaction mixture is shaken with 15 ml of a 5% aqueous sodium carbonate solution under ice cooling, and the lower organic phase is separated. The aqueous alkaline phase is extracted thrice with 10 ml of a 99:1 mixture of dichloromethane and methanol, each. The organic phases are combined, dried over anhydrous magnesium sulfate, filtered, and the filtrate is evaporated to dryness in vacuo. The resulting 1.00 g of oily substance, which is a mixture of 15-epimers, can be used in the next step of the synthesis without purification.

The mixture of 15-epimers can be subjected to preparative layer chromatography (adsorbent: KG-PF$_{254+366}$ grade silica gel, solvent: a 14:3 mixture of benzene and methanol, eluting agent: a 2:1 mixture of acetone and dichloromethane) to separate the individual isomers.

0.32 g (30.5%) of an isomer with lower $R_f$ value (isomer "A") are obtained; m.p.: 215°–216° C. (after recrystallization from acetone).

IR (KBr): 1705 cm$^{-1}$ (lactam CO).

Analysis: calculated for $C_{20}H_{22}N_2OBrCl$ (mol.wt.: 421.77): C: 56.95%, N: 6.64%, H: 5.25%; founnd: C, 56.70%, N: 6.45%, H: 5.35%.

$[\alpha]_D^{25} = +55.6°$ (c=1.024%, in chloroform).

The separation yields 0.45 g (43%) of the isomer with higher $R_f$ value (isomer "B") as an oily substance. This substance is treated with methanolic hydrochloric acid, and the resulting hydrochloride is crystallized from acetone. The hydrochloride melts at 269° C. under decomposition.

IR (KBr): 1705 cm$^{-1}$ (lactam CO).

Analysis: calculated for $C_{20}H_{23}N_2OBrCl_2$ (mol.wt.: 458.23): C: 52.41%, H: 5.05%, N: 6.11%; found: C: 52.34%, H: 5.27%, N: 6.20%.

$[\alpha]_D^{25} = 0°$ (c=1.05%, in dichloromethane).

EXAMPLE 4

(+)-3(S),17(S)-11-Bromo-14-oxo-15-hydroxyimino-E-homoeburnane 0.50 g (1.18 moles) of (+)-3(S),17(S)-11-bromo-14-oxo-15-chloro-E-homoeburnane (mixture of 15-epimers, prepared as described in Example 3) are dissolved in 11 ml of glacial acetic acid, a solution of 2.70 g of sodium nitrite in 9 ml of water is added dropwise to the stirred mixture at room temperature, and the resulting mixture is allowed to stand at room temperature for 30 hours. Thereafter the mixture is poured into 20 g of ice water, the pH of the mixture is adjusted to 9 with concentrated aqueous ammonia, and the alkaline solution is extracted thrice with 10 ml of dichloromethane, each. The organic phase is separated, dried over anhydrous magnesium sulfate, filtered, and the filtrate is evaporated. The oily residue, weighing 0.50 g, is purified by preparative layer chromatography (adsorbent: KG-PF$_{254+366}$ grade silica gel, solvent: a 14:3 mixture of benzene and methanol, eluting agent: a 20:4 mixture of dichloromethane and methanol). The $R_f$ value of the starting substance is higher than that of the end-product.

0.32 g (60.5%) of the title compound are obtained as an oily substance. This substance is treated with methanolic hydrochloric acid to obtain the respective hydrochloride to a crystalline solid melting at 235°–236° C. (from methanol).

IR (KBr): 3460 (OH), 1710 (lactam CO), 1622 (C=N) cm$^{-1}$.

Mass spectrum: m/e (%): 415 (M+,62).

$[\alpha]_D^{25} = +44.9°$ (c=1.10%, in dimethyl formamide).

What we claim is:

1. A halogenated 15-hydroxy-E-homoeburnane of the formulae (Ia) or (Ib),

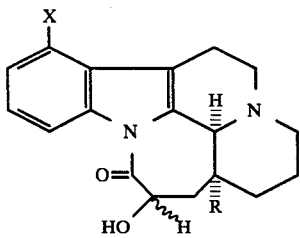
(Ia)
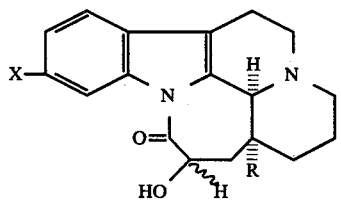
(Ib)
wherein R is a $C_{1-6}$ alkyl group and X is halogen, or an acid addition salt or optically active isomer thereof.
2. (±)-9-Bromo-14-oxo-15-hydroxy-E-homoeburnane-(3α,17α) as defined in claim 1.
3. (±)-11-Bromo-14-oxo-15-hydroxy-E-homoeburnane-(3α,17α9 as defined in claim 1.
4. (±)-3(S),17(S)-9-Bromo-14-oxo-15-hydroxy-E-homoeburnane as defined in claim 1.
5. (+)-3(S),17(S)-11-Bromo-14-oxo-15-hydroxy-E-homoeburnane as defined in claim 1.
* * * * *